United States Patent [19]

Powell

[11] Patent Number: 5,646,298

[45] Date of Patent: Jul. 8, 1997

[54] CYCLOPROPYLINDOLE PRODRUGS

[75] Inventor: Michael J. Powell, Danville, Calif.

[73] Assignee: ProCoron, Inc., Danville, Calif.

[21] Appl. No.: 482,753

[22] Filed: Jun. 7, 1995

[51] Int. Cl.$^6$ .................. C07D 209/56; C07D 405/14

[52] U.S. Cl. .................. 548/427; 548/430; 548/433; 548/311.7; 548/181; 548/455; 548/490; 548/491

[58] Field of Search .................. 548/427, 430, 548/433, 311.7, 181, 455, 490, 491; 514/411, 397, 365, 414, 415

[56] References Cited

U.S. PATENT DOCUMENTS 4,708,929  11/1987  Henderson .................. 435/7

FOREIGN PATENT DOCUMENTS 4415463  11/1995  Germany.

OTHER PUBLICATIONS

CA 124: 145899p Preparation of ... prodrugs. Tietz, 1995.

Primary Examiner—Joseph McKane
Attorney, Agent, or Firm—Isaac Angres

[57] ABSTRACT

The present invention describes cyclopropylindole cytotoxic prodrugs of formulas (I), (II) and (III) as shown in the specification. The present invention is also directed to a method for the site-specific treatment of neoplastic diseases in a mammal which method includes the following steps: (i) administering to an afflicted mammal an effective amount of a targeting agent- enzyme donor peptide conjugate wherein the targeting agent is selected from the group of antibodies, monoclonal antibodies, adhesion molecules and tumor cell surface binding ligands; (ii) administering to the afflicted mammal an effective amount of an enzyme acceptor dimer thereby forming active enzymatic sites at a tumor cell surface; and (iii) administering to the afflicted mammal a therapeutically effective amount of an enzyme-activateable, cytotoxic pro-drug thereby releasing the cytotoxic drug at the tumor site.

8 Claims, 2 Drawing Sheets

CYCLOPROPYLINDOLE PRODRUGS

FIELD OF THE INVENTION

The present invention relates to novel prodrugs of cytotoxic agents and their therapeutic use. Furthermore, The present invention generally relates to novel prodrugs of cytotoxic compounds containing cyclopropyl indole moieties. More specifically, the invention relates to novel prodrugs comprising analogs of CC-1065, duocarmycins and derivatives of CC-1065, duocarmycins and their therapeutic use. Additionally, the present invention relates to cytotoxic prodrug derivatives incorporating glycosyl moieties. The novel prodrugs have therapeutic use as a result of enzymatic activation either by enzymes that have been selectively targeted to a specific cell population through the use of specific cell binding agent such as enzyme conjugates or by enzymes that are indigenous to the specific cell population.

BACKGROUND OF THE INVENTION (+)-cc-1065 (C. G. Chidester et. al., *J. Amer. Chem. Soc.*, 103, 7629 (1981)) and the duocarmycins (Duocarmycin SA: M. Ichimura et al., *J. Antibiot.*, 1990, 43, 1037; M. Ichimura et al., *J. Antibiot.*, 1991, 44, 1045; Duocarmycin A, $B_1$, $B_2$, $C_1$ and $C_2$: M. Ichimura et al., *J. Antibiot.*, 1988, 41, 1285; I. Takehashi et. al., *J. Antibiot.*, 1988, 41, 1915; T. Yasuzawa et. al., *Chem. Pharm. Bull.*, 1988, 36, 3728; T. Ogawa et al., *J. Antiobiot.*, 1989, 42, 1299; Pyrindamycin A and B: Ohba et al., *J. Antiobiot.*, 1988, 41, 1515; S. Ishii et al., *J. Antiobiot.*, 1989, 42, 1713) constitute exceptionally potent naturally occurring antitumor antibiotics, isolated from Streptomyces species that heve been shown to be related through their common participation in a characteristic minor grrove adenine N3 alkylation duplex DNA ( M. A. Warpehoski et. el., *Chem. Res. Toxicol.*, 1988, 1, 315; L. Hurley et al., *Acc. Chem. Res.*, 1986, 19, 230; D. L. Boger in Advances in *Heterocylic Natural Product Synthesis*, Vol. 2, W. H. Pearson; Ed., JAI Press, Greenwich, 1992, 1–188; D. L. Boger, *Chemtracts: Org. Chem.*, 1991, 4, 329; R. S. Coleman and D. S. Boger in *Studies in Natural Products Chemistry*; Atyta-ur-Rahman, Ed., Elsevier, Amsterdam, 1989, Vol.3, 301; V. H. Rawal et. el., *Heterocycl.*, 1987, 25, 701).

Since the disclosure of the structure of (+)-CC-1065, the agent and structural analogs have been the subject of continued synthetic as well as biological studies. Numerous synthetic analogs of CC-1065 and the duocarmycins have been synthesized incorporating deep-seated changes in the alkylating subunit with the intent of determining the fundamental structural features contributing to the polynucleootide recognition and funtional reactivity (D. L. Boger et al., Pure & Appl. Chem., 1993, 65, 1123; D. L. Boger et al., J. Amer. Chem. Coc., 992, 114, 9318; J. Amer. Chem., Soc., 1992, 114, 5487; D. L. Boger et al., Proc. Natl. Acad. Sci. USA, 1991, 88, 1431; D. L. Boger et al., Bioorg. & Med. Chem. Letts, 1991, 1, 55; J. Amer. Chem. Soc., 1992, 112, 5230; J. Org. Chem., 1990, 55, 5823; J. Org. Chem., 1989, 54, 1238; M. A. Warpehoski et al., J. Med. Chem., 1988, 31, 590). The cytotoxic potency of CC-1065 has been correlated with the alkylating activity and DNA-binding or DNA-interchelating activity of CC-1065. The two activities reside in two separate pads of the molecule. The alkylating activity is contained in the CPI unit A (cyclopropapyrroloindole unit) and the DNA-binding in the two subunits of the molecule.

CC-1065 is 100 to 1000-fold more cytotoxic than conventional cancer chemotherapeutic agents such as duanorubicin, vincristine and methotrexate (B. K. Bhuyan et al., Cancer Res., 1982, 42, 3532). Although CC-1065 showed moderate anti-tumor activity in vivo, it was not evaluated clinically because it caused delayed deaths in mice at therapeutic doses (J. P. McGovren et al., J. Antibiot., 1984, 37, 63; V. L. Reynolds et al., J. Antibiot., 1986, 39, 319). The synthesis of new analogs of CC-1065 that retain the high in vitro cytotoxicity of the parent drug without causing delayed lethality in mice have been reported (M. A. Warpehoski et al., J. Med. Chem., 1988, 31, 590–603). Adozelesin (U-73975) is one of many CC-1065 analogues with excellent broad-spectrum anti-tumor activity in vivo without causing delayed deaths (L.H. Li et al., Invest. New Drugs, 1991, 9, 137).

The high toxicity of CC-1065 and the related duocarmycins has prompted the synthesis of prodrug analogues. Ester and urethane analogs of the CPI phenol of the chloromethyl precursor to the cyclopropyl function typified by Carzelesin (U-80244) (FIG. 4) have proved to be more efficacious in vivo than the parent CPI drugs (L. H. Li et al., Cancer Res., 1992, 52, 4904). Hydrolysis of such esters or urethanes to reform the chloromethyl phenol compound must occur prior to the ring-closure reaction, in order to produce the DNA-reactive cyclopropyl keto compound. A similar prodrug strategy was recently reported for Duocarmycin B2 (H. Ogasawara et al., in Proceedings of the 85th Annual Meeting of the American Association for Cancer Research, Abstract 2325, p390, 1994).

The use of tumor specific antibodies to the targeted delivery of enzymes to the surface to tumor cells in combination with specific enzyme activated prodrugs has been employed in an effort to improve the therapeutic efficacy of a number of cytotoxic drugs. Prodrugs derived from etoposide and mitomycin C in combination with alkaline phosphatase antibody conjugates (P. D. Senter et al., Proc. Natl. Acad. Sci. USA. 1988, 85, 4842; P. D. Senter et al., Cancer Res. 1989, 49, 5789; H. J. Haisma et al., Cancer Immunol. Immunotherap., 1992, 34, 343); bifunctional alkylating agents and carboxypeptidase G2 (C. J. Springer et al., Eur. J. Cancer, 1991, 27 (11), 1361) and bacterial β-glucuronidase (S. -M. Wang et al., Cancer Res., 1992, 52, 4484); vinca alkaloids and β-lactamase (D. L. Meyer et al., Cancer Res., 1993, 53, 3956); and methoxtrexate and carboxypeptidase A (E. Haenseler et al., Biochemistry, 1992, 31, 891) have been reported in the recent literature. This antibody directed enzyme prodrug therapy, "ADEPT" approach has demonstrated efficacy both 'in vivo' and in 'in vivo' animal model studies. A glucuronide spacer prodrug derivative of doxorubicin has been employed together with a hymanized carcinoembryonic antigen-specific recombinant variable region fused to human β-glucuronidase in an 'in vivo' study with nude mice bearing human CEA expressing tumor zenografts. The two component fusion protein/prodrug system showed therapeutic effects superior to those of conventional chemotherapy (K. Bosslet et al., Cancer Res., 1994, 54, 2151).

Additionally, mAb-enzyme conjugates have been used for the site-specific formation of cytotoxic agents. The principle advantage of this approach compared to those involving the direct attachment of a cytotoxic agent to a mAb is that the targeted enzyme can greatly amplify the number of drug molecules delivered to each tumor cell. Furthermore, the cytotoxic effect may not be restricted to only those tumor cells that have bound the conjugate, since the drug is released extracellularly and may be able to migrate to neighboring tumor cells. The principle disadvantage lies in the approach's inherent complexity, since two separate agents and an appropriate time interval between their respective administrations are required for therapeutic efficacy.

Mab-enzyme conjugates can release a vast array of cytotoxins ranging from clinically approved anticancer drugs to highly potent agents that would have little chance for success in the clinic if given systemically. Several groups have demostrated that significant in vitro and in vivo antitumor activities can be obtained using this approach, and clinical studies are now underway. Further refinements in the technology, such as the use of recombinant fusion proteins comprises of relatively nonimmunogenic components, the development of prodrugs with optimal pharmacological distributions and minimal toxicities, and strategies to achieve high tumor to normal tissue conjugate ratios, may provide the basis for making this approach clinically useful.

The use of enzyme-acceptor and enzyme-donor polypeptides in enzyme complementation assays is described in U.S. Pat. No. 4,708,929. The prior art is silent on the use of this technology in the generation of cytotoxic agents by targeted enzymes.

SUMMARY OF THE INVENTION

Figure 1:
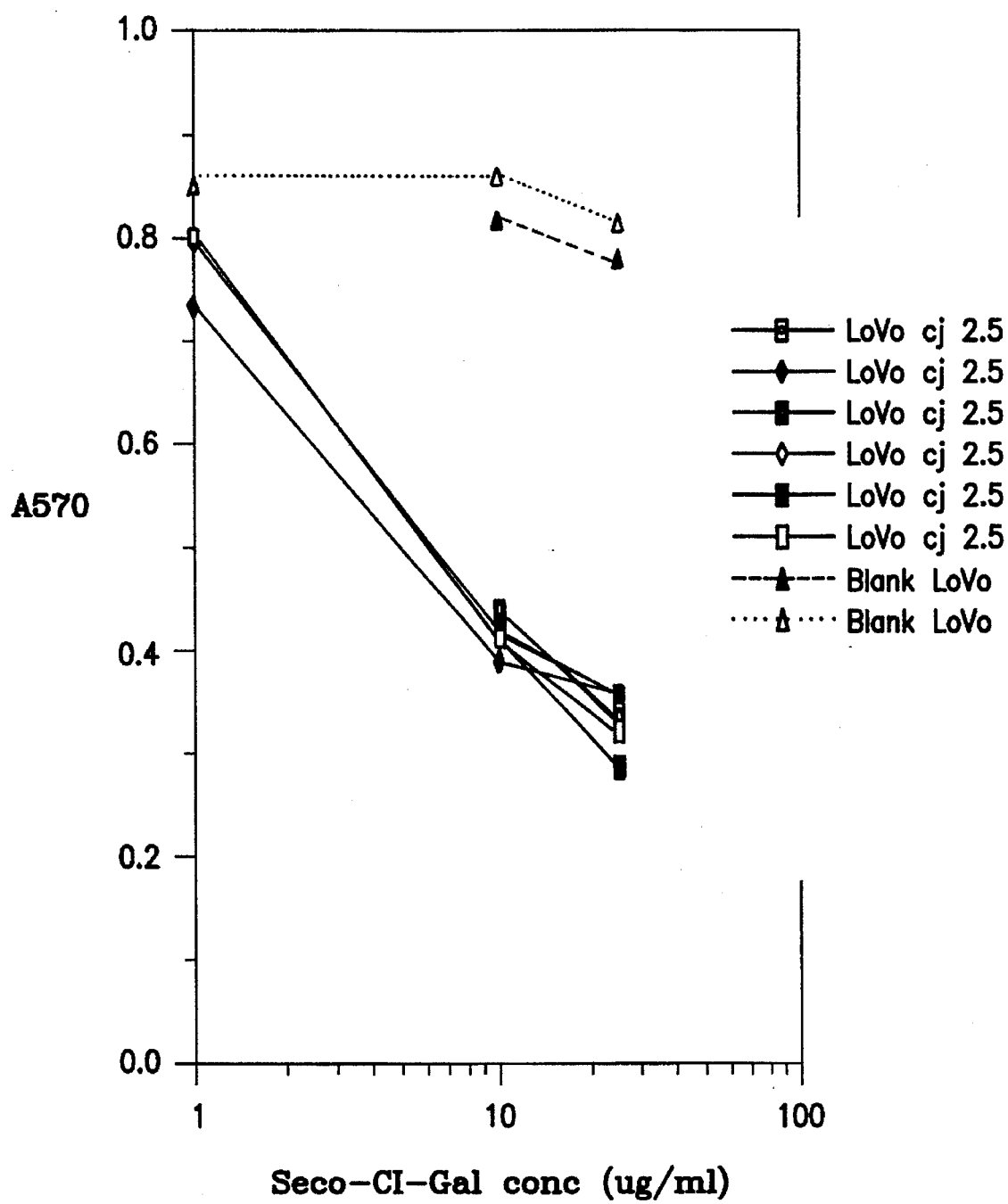
FIG. 1 shows the cytotoxic effect of Gal-Cl on LoVo cells incubated with T84.66-βgal conjugate.

The present invention provides novel analogues and derivatives of CC-1065 and Duocarmycins that can be activated either by exogeneously administered monoclonal antibody-enzyme conjugates or genetic fusion proteins or by lysosomal enzymes released as a result of tumor necrosis.

The present invention also provides improved therapeutic efficacy as a result of using the prodrug analogues of the present invention. The improved prodrugs of the present invention are obtained by introducing a glycosyl moiety.

The instant invention also provides glycosyl modified prodrugs which when used in conjunction with enzyme-monoclonal antibody conjugates will selectively deliver lethal levels of drugs to tumors.

The present invention further provides targeted delivery of prodrugs using enzyme-acceptor and enzyme-donor polypeptides prepared by recombinant DNA means or chemical polypeptide synthesis.

DESCRIPTION OF THE PREFERRED EMBODIMENTS

The present invention is directed to compounds having the following structure (I):

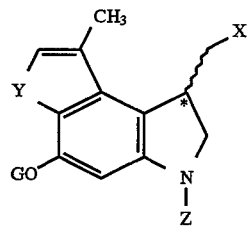

wherein G is a glycosyl moiety; Y is selected from the group consisting of O and NH; X is selected from the group consisting of Cl, Br, or —OSO₂CH₃ and Z is selected from the group consisting of —SO₂—CH₃ and —C(O)—R where R is selected from the group consisting of —NHNH₂,

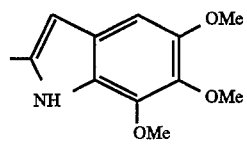

Trimethoxyindole- TMI,

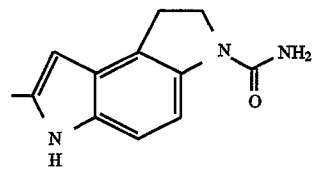

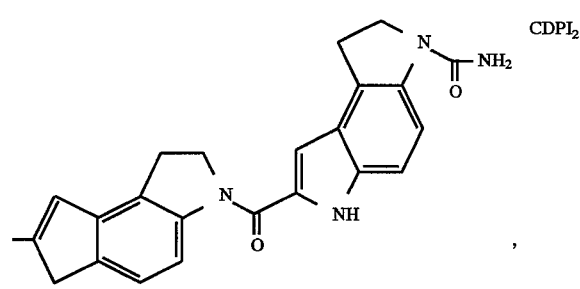

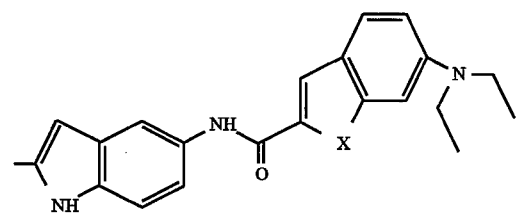

where X=NH, O or S,

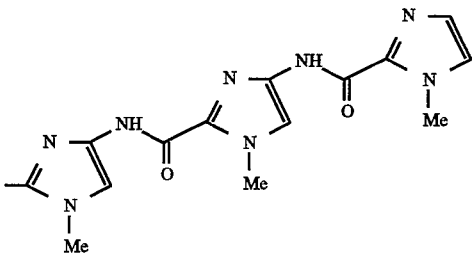

and

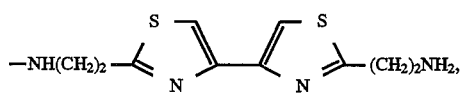

wherein the asterisk (*) represents an assymmetric carbon giving rise to all optically-active and non-optically-active stereoisomers, as well as racemic and non-racemic mixtures. The glycosyl moiety is typically selected from the group consisting of β-galactopyranosyl, β-glucopyranosyluronate (β-glucuronyl) and α-mannopymnosyl. When Y is NH the inventors refer to such compounds as Seco-CPI prodrugs and when Y is O they are known as Seco-CFI prodrugs. The above abreviations will be used throughout the present specification. It is within the contemplation of the present invention that the class of compounds of the structure (I) include the optically-active isomers, non-racemic mixtures, racemic mixtures, as well as all the possible stereoisomers.

Additionally, the present invention is directed to compounds having the formula (II):

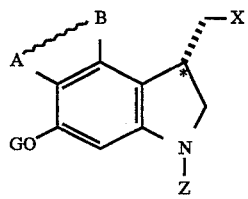

wherein G is a glycosyl moiety, A and B are selected such that when not connected they are both hydrogens and when connected A and B represents a fused benzene ring; X is selected from the group consisting of Cl, Br, or —OSO$_2$CH$_3$ and Z is selected from the group consisting of —SO$_2$—CH$_3$ and —C(O)—R where R is selected from the group consisting of —NHNH$_2$,

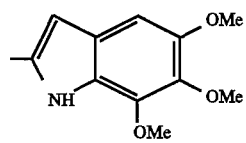

Trimethoxyindole- TMI,

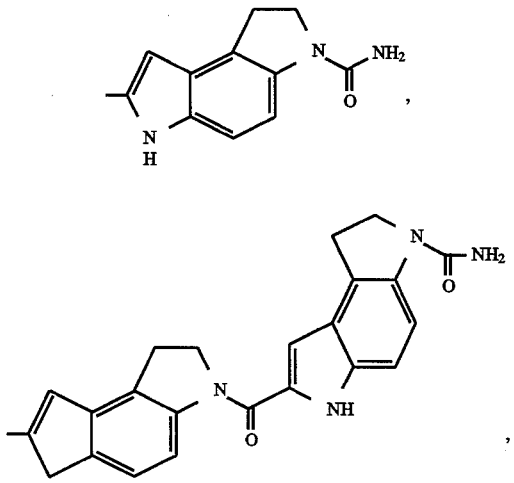

where X=NH, O or S,

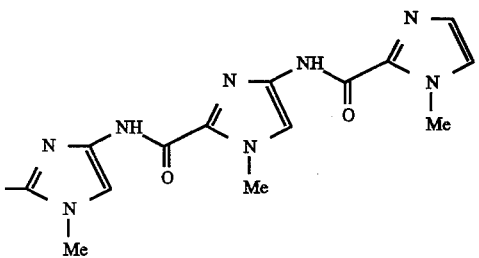

and

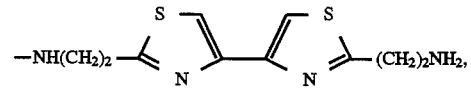

wherein the asterisk (*) represents an assymmetric carbon giving rise to all optically-active and non-optically-active stereoisomers, as well as racemic and non-racemic mixtures.

G is typically a glycosyl moiety selected from the group consisting of β-galactopyranosyl, β-glucopyranosyluronate (β-glucuronyl) and α-mannopyranosyl. As noted above, when A and B are not connected then both A and B are hydrogens and when A and B are covalently connected they represent a fused benzene ring. When A and B are both hydrogens, the inventors refer to this compounds as Seco-CBI prodrug while when A and B form a fused benzene ring they are knowns as Seco-CBI.

Furthermore, the present invention is directed to compounds of the formula (III):

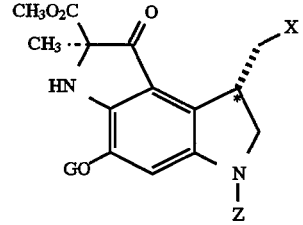

wherein G is a glycosyl moiety; X is selected from the group consisting of Cl, Br, or —OSO$_2$CH$_3$ and Z is selected from the group consisting of —SO$_2$—CH$_3$ and —C(O)—R where R is selected from the group consisting of —NHNH$_2$,

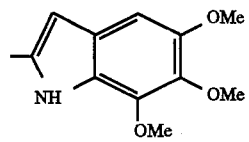

Trimethoxyindole- TMI,

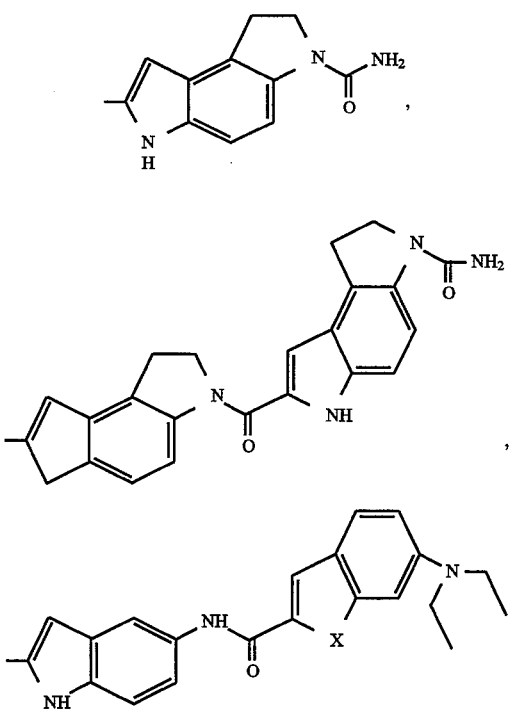

where X=NH, O or S,

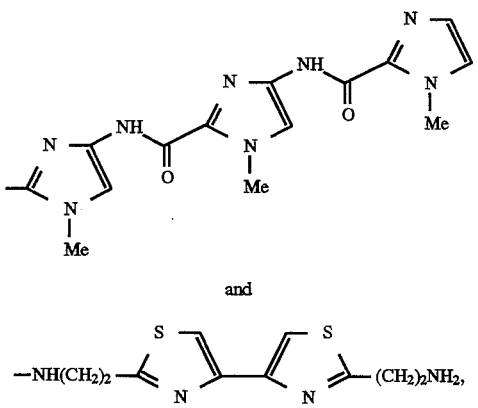

wherein the asterisk (*) represents an assymmetric carbon giving rise to all optically-active and non-optically-active stereoisomers, as well as racemic and non-racemic mixtures. In the compounds of formula (III) G is a glycosyl moiety selected from the group consisting of β-galactopyranosyl, β-glucopyranosyluronate (β-glucuronyl) and α-mannopyranosyl. When X=Cl the above compound is referred to as Duocarmycin $C_2$ prodrugs and when X=Br the compounds are known as Duocarmycin $B_2$ prodrugs.

The compounds of the present invention are prepared by conventional organic synthesis. More specifically, the compounds are prepared by reacting the appropriate 6-hydroxysubstituted,2,3-dihydro-1H-indole with acetobromogalactose under reflux in a solvent medium such as chloroform in the presence of a base such as KOH and tetrabutyl ammonium hydroflusulfate and then removing the acetyl protecting groups. Further synthetic details reagrding the prodrugs of the present invention can be found in the Examples of the present invention.

The compounds of the present invention are particularly useful in the treatment of cancer. The present inventors have found that the therapeutic efficacy of CC-1065 and duocarmycins, and analogs thereof can be improved by the use of prodrugs analogues of the present invention. The in vivo biodistribution of these therapeutic agents is changed through the targeted activation of the prodrug at tumor sites.

The present invention is also directed to a method for the site-specific treatment of neoplastic diseases in a mammal which method includes the following steps: (i) administering to an afflicted mammal an effective amount of a targeting agent- enzyme donor peptide conjugate wherein the targeting agent is selected from the group of antibodies, monoclonal antibodies, adhesion molecules and tumor cell surface binding ligands; (ii) administering to the afflicted mammal an effective amount of an enzyme acceptor dimer thereby forming active enzymatic sites at a tumor cell surface; and (iii) administering to the afflicted mammal a therapeutically effective amount of an enzyme-activateable, cytotoxic prodrug thereby releasing the cytotoxic drug at the tumor site.

Another preferred embodiment of the present invention is a method for site-specific treatment of neoplastic diseases in a mammal which includes the following sequential steps:
(i) administering to an afflicted mammal an effective amount of an antibody-enzyme donor peptide conjugate;
(ii) administering to the afflicted mammal an effective amount of an enzyme acceptor dimer thereby forming active enzymatic sites at the tumor cell surface; and
(iii) administering to the afflicted mammal a therapeutically effective amount of an enzyme activatable cytotoxic prodrug thereby releasing the cytotoxic drug at the tumor site.

The contemplated targeted therapy of the present invention is practiced as follows: An enzyme donor peptide (α-peptide. ED )derived from E. Coliβ-Galactosidase is attached to an antibody that is specific for an antigert expressed on the surface of the cancer cells. The enzyme donor peptide can be attached by standard chemical conjugation techniques or via genetic engineering techniques. The above conjugate is administered to the patient and the antibody peptide conjugate is targeted to the tumor cells in the body. Since the peptide is relatively small, M.W. ca. 10,000 and is attached preferably to the Fab' fragment ( M.W. 50,000 ) or more preferably to a recombinant single chain Fv ( M.W. 27,000 ) derived from the parent IgG, the antibody peptide conjugate should be cleared rapidly from the circulation; most probably by excretion through the kidneys. Thus a relatively high tumor/blood ratio is achievable in a short space of time. After a suitable period of time the enzyme acceptor (EA) dimer fragment derived from a β-Galactosidase of M.W. ca. 200,000, it is administered as a wild-type non-covalent associated dimer or as a genetically engineered single chain dimeric molecule scEA. This EA protein will associate with the tumor cell surface bound ED Mab conjugate to create active β-Galactosidase at the tumor cell surface. A prodrug such as those of formula I, II or III containing a galactosyl moiety is then administered and is converted into the cytotoxic agent at the surface of the tumor cell, thus targeting the cytotoxic agent specifically to the tumor and reducing the systemic toxicity that is often seen with anti-cancer drugs. The use of recombinant enzyme fragments are of course also contemplated by the present invention.

The enzyme donor polypeptides and enzyme acceptor polypeptides sultable for use in the practice of the present invention are prepared by the techniques described in Henderson U.S. Pat. No. 4,708,929 whose entire contents are incorporated by reference therein.

The donor polypeptides and acceptor polypeptides themselves are enzymatically inactive; however when reacted together in aqueous medium they associate to form a catalytically active enzyme via a phenomenom known as complementation. The polypeptides which can be used include fusion proteins, genetically engineered polypeptides, and chemically synthesized polypeptides. Additionally, humanized and chimeric antibodies can be used, as well as Fab and (Fab)$_2$ antibody fragments. The antibody enzyme donor can also be a donor fusion protein or a recombinant fusion protein.

Figure 2:
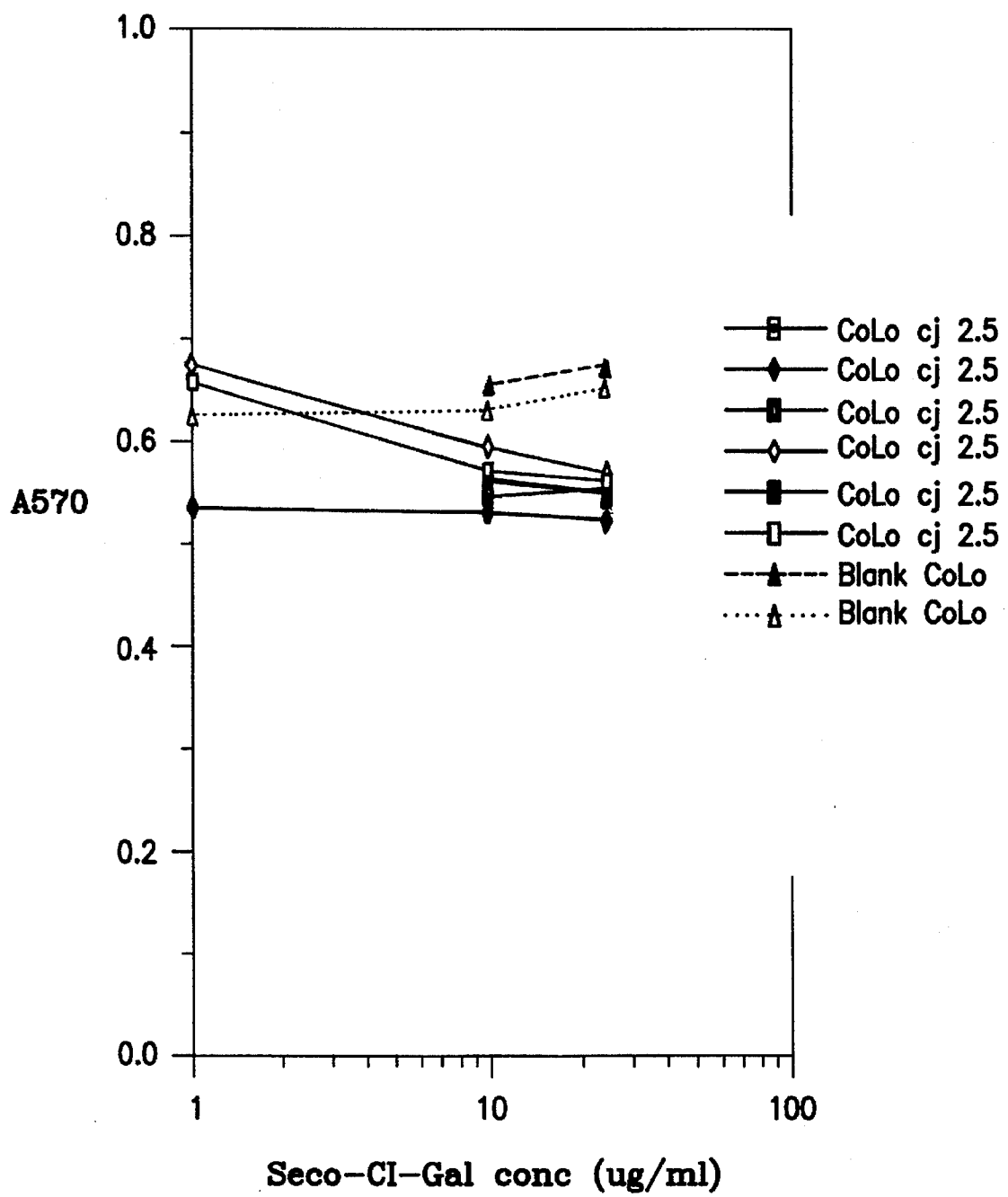
FIG. 2 illustrates the cytotoxic effect of Gal-Cl on Colo cells incubated with T84.66-βgal conjugate.

The prodrugs and their enzyme-mAb conjugates are evaluated for cytotoxic potential first with tumor cells in vitro, and subsequently by studies with tumor xenografts in nude mice. Prior to in vitro testing, however it is worthwhile to determine the capability of the enzyme to produce lethal concentrations of drug from the prodrug. In vitro cytotoxicity measurements are conducted by treating tumor cells with excess conjugate, followed by extensive washing of the cells and their exposure to varying concentrations of prodrug. Cells not treated with conjugate but exposed to rpodrug or parent drug serve as controls. The results of cytotoxicity experiments for the prodrugs of the present invention are illustrated in FIGS. 1 and 2.

EXPERIMENTAL

The following are illustrative Examples of the present invention:
A. Synthesis of Cl Based Prodrugs

EXAMPLE 1

(1) 6-(Benzyloxy)-3-[(diphenyl-tert-butyl-silyl) oxymethyl]-1-(methylsulfonyl)-2,3 dihydro-1H-indole A mixture of 6-(Benxyloxy)-3-(hydroxymethyl)-1-(methylsulfonyl)-2,3 dihydro-1-H-indole (synthesized as described in L. F. Tietze et al., Chem. Bet., 1994, 126, 2733) 2.17 g, 6.52 mmol), diphenyl-tert-buty-silylchloride (1.81 ml, 1.91 g, 7 mmol), triethylamine (3 ml) and 2-dimethylaminopyridine DMAP (85 mg, 0,7 mmol) were incubated 24 h at room temperature under an atomosphere of dry argon. A further 0.9 ml of the silylchloride was added and the reaction incubated for a further 24 h period. Solvent was removed 'in vacuo' and the residual oil purified by flash chromatography on silica gel 60 eluting with ethyl acetate/hexane (1:4). The product was obtained as an oil; yield 3.59 g (94%).

EXAMPLE 2

(2) 3-[Diphenyl-tert-butyl-silyl)oxymethyl]-6-hydroxy-1)methylsulfonyl)-2,3 dihydro-1H-indole The oily product obtained as described in (1) (3.3 g, 5.78 mmol) in ethyl acetate (15 ml) and 10% Pd/C(700 mg) was hydrogenated under 3 bar of hydrogen pressure celite. The solvent was evaporated 'in vacuo' and the crude product purified by flash chromatography on silica eluting with ethyl acetate/hexane (4:7). The crystalline product obtained yield 2.56 g. m.p. 153° C.

EXAMPLE 3

(3) 3-[(Diphenyl-tert-butyl-silyl)oxymethyl]-1-(methylsulfonyl)-2,3-dihydro-1H-6-yl-(2,3,4,6-tetra-O-acetyl)-β-D-galactopyranoside.

EXAMPLE 4

(4) 3-(Chloromethyl)-1-(methylsulfonyl)-2,3-dihydro-1H-6-yl-β-D-galacto-pyranoside. (Seco Cl-galactoside)

The tetra-O-acetyl-galactoside isolated in (3) (280 mg, 345 mmol) and tetrabutylammonium fluroide (220 mg, 0.7 mmol) in tetrahydrofuran was stirred for 10 min. at room temp. Solvent was removed 'in vacuo' and the crude product purified by chromatography on deactivated silica gel eluting with ethyl acetate/hexane (2:1) to yield 162 mg (79%). This was mixed with dichloromethane (10 ml) and tetrachloromethane (10 ml) and triphenylphosphane (225 mg, 0.84 mmol) was stirred at reflux for 8 h under dry argon. A further quantity of triphenylphosphane (225 mg, 0.84 mmol) was added and refluxed a further 4 h. Evaporation of the solvent at room temperature 'in vacuo' and flash chromatography (30 g silica gel), ethyl acetate/hexane (2:1) eluent afforded the chloride (170 mg, 98%). The chloride was dissolved in anhydrous methanol (3 ml) and anhydrous potassium carbonate (10 mg) added. After stirring 10 min. at room temperature the reaction mixture was filtered and evaporated to afford seco-Cl-galactoside as a white solid (52.4 mg, 87%).
B. CBI Based Prodrugs

EXAMPLE 5

(5) 5-(Benzyloxy)-3-(tert-butyloxycarbonyl)-1-[(diphenyl-tert-buty-silyl)oxymethyl]-1,2-dihydro-3H-benz[e] indole This was synthesized essentially as described for the Cl based analog in A (1) above from 5-(Benzyloxy)-3-(tert-butyloxycarbonyl)-(hydroxymethyl)-1,2-dihydro-3H-benz[e) indole (synthesized as described in D. L Boger et al., J. Org. Chem., 1992, 57, 2873-2876). The product was obtained as a pale yellow oil (96% yield).

EXAMPLE 6

(6) 1-(Diphenyl-tert-butyl-silyl)oxymethyl]-5-hydroxy-3-(tert-butyloxycarbonyl)-1,2-dihydro-3H-benz[e] indole Obtained by hydrogenolysis of the above product in ethyl acetate and 10% Pd/C.

EXAMPLE 7

(7) 1-[(Diphenyl-tert-butyl-silyl) oxymethyl]-5-hydroxy-3-[(5,6,7-trimethoxyindol-2-yl)carbonly]-1, 2-dihydro-3H-benz [e] indole The phenol derived in (2) was treated with anhydrous 3M HCl-EtOAc for 30 min. at room temperature solvent was removed in vacuo and the crude product obtained dissolved in DMF and treated with [3-(dimethylamino) propyl]-ethylcarbodiimide hydrochloride (EDCI and 5,6,7-trimethoxyindole-2-carboxylic acid and stirred for 24 hr. at room temperature. The solution was diluted with water and extracted with EtOAc. The organic layer was washed with 1N aqueous Hcl, saturated sodium bicarbonate solution and saturated aqueous NaCl, dried (sodium sulfate) and concentrated. Flash chromatography on silica gel eluting with EtOAc-hexane afforded the product as a pale yellow solid in 91% yield.

EXAMPLE 8

(8) 1-[(Diphenyl-tert-butyl-silyl)oxymethyl]-5-(2,3, 4,6-tetra-O-acetyl)-β-D-galactopyranosyl-3-[(5,6,7-trimethoxyindole-2-yl)carbonyl]-1,2-dihydro-3H-benz [e] indole Prepared from the product obtained in (3) essentially as described for the related Cl based analog in A (3) above.

EXAMPLE 9

(9) 1-(Chloromethyl)-5-β-D-galactopyranosyl-3-[(5, 6,7-trimethxyindol-2-yl)carbonyl]-1,2-dihydro-3H-benz [e] indole (seco-CBI-TMI galactoside)

Prepared from the product obtained in B (4) essentially as described for the Cl related analog in A (4) above.

C. Preparation of Mab β-Galactosidase Conjugate

EXAMPLE 10

Mab T84.66 (5 mg/ml) in 100 mM phosphate buffer pH 7.0 was treated with succinimidyl-maleimido-cyclohexane carboxylate (SMCC) solution (0.278 mg) 25 fold molar excess over IgG) in DMF. After incubating for 2 h at room temp. the modified Mab was exchanged into 100 mM phosphate buffer, 5 mM EDTA pH 6.0 employing a PD10G25 cartridge, β-Galactosidase (6 mg) Boehringer Mannheim Biochemicals was added to the Mab solution so that the molar ratio of IgG to enzyme was 3:1. After incubating at 4° C. overnite the conjugate was purified by gel filtration on a Superdex 200 column employing 100 mM PIPES, 100 mM NaCl, 10 mM EGTA, 1 mM EDTA, 5 mM Mg(OAc), pH 6.8. The pooled conjugate fractions were sterilized by filtration through a gelman filtration membrane and stored at 4° C.

D. In Vitro Tumor Cell Targeting Assay (i) Cell Culture

CoLo 320 DM (ATCC #CCL-220) and LoVo (ATCC #CCL-229) adenocarcinoma cell lines were obtained from Amedcan Type Culture Collection (ATCC Rockville, Md.). CoLo cell line was maintained in RPMI 1640 plus 10% heat inactivated Fetal Bovine Serum (Gibco, Grand Island, N.Y.). LoVo cell line was maintained in Ham's F12 medium with Kaighn's modification plus 20% FBS (Gibco). The cells were cultured in plastic tissue culture flasks (Coming) at 37° C. under humidified 5% $CO_2$/95% air. The medium was renewed every 2–3 days. Confluent culture were treated with 0.25% trysin, 0.02% EDTA in $Ca^{2+}$ and $Mg^{2+}$ free phosphate buffered saline (PBS pH 7.4) (Gibco for 10 minutes and subcultured at a 1:3 split ratio.

(ii) MTT Cytotoxicity studies were performed using a colorimetric assay involving the reduction of the tetrazolium salt MTT to a blue insoluble crystal by mitochondria dehydrogenase activity. Intracellular crystal formation occurs in quantities directly correlated to cell number. MTT cytotoxicity assays (Promega Corp., Madison, Wis.) were performed essentially as described (T. Mosmann, *J. Immunol. Methods*, 1983, 65, 55; H. Tada et al., *J. Immunol. Methods*, 1986, 93, 157; M. B. Hansen et al., *J. Immunol. Methods*, 1989, 119, 203; M. Niks et al., *J. Immunol. Methods*, 1990, 130, 149). All assays were conducted in 96 well microtiter tissue culture plates (Coming). Each well was seeded with approximately $10^3$–$10^4$ cells (in 100 μl) at the start of a timed experiment and allowed to proliferate overnight. Next morning 90 μl of the medium was replaced with Hanks Buffered Salt Solution (HBSS), Minimal Essential Media (MEM), or rich media (either 90% RPMI 1640 with 10% FBS for CoLo cell line or 80% Ham's F12 plus 20% FFBS for LoVo cell line).

To each well 10 μl of various concentrations of activated prodrug or unactivated prodrug in HBSS was added. Activation of the prodrugs was performed by pretreating prodrug stock solutions with appropriated glycosidase enzyme (10 μl, 10 μg/ml): e.g., for seco-Cl-Gal (Example 4 above) *E. coil*β-galactosidase (Boehringer Mannheim, Indianapolis Ind.) was employed.

Media containing fresh dilutions of the cytotoxic agent 4-Hydroperoxy-cyclophosphamide (CAP) (ASTA Medica, Germany) was included in some experiments as a positive control. Cells were incubated overnight in the presence of the drug. 15 μl of MTT dye dye stock solution was then added to each well. After 4 hours 100 μl off stop/solubilization solution was added. Microtiter plates were incubated overnight in a sealed container to permit the complete solubilization of the MTT crystals. Absorbances (A570) were read on a Bio-Rad 3550 microplate reader.

(iii) Targeted Prodrug Activation by Tumor Antigen Specific Monoclonal Antibody Enzyme Conjugate.

Human adenocarcinoma cells Colo 320 DM (CEA antigen negative) and LoVo (CEA antigert positive) were grown in amicrotiter plate and any non-adherent cells washed away with growth medium. The adherent cells were incubated with T84.66 enzyme conjugate (2.5 mg/ml) for 1 h at room temperature. The cells were then washed 3× with HBSS and various concentrations of prodrug added to the wells in order to ascertain the IC50 value. After 24 h live cells remaining were measured employing a dye binding assay. Results are shown in FIGS. 1 and 2.

These results indicate specific glycoside prodrug activated targeted killing of CEA positive human adenocarcinoma cells by an anti-CEA Mab-glycosidase conjugate. The IC50 for seco-Cl-Gal was found to be 5 μg/ml/. The CBI based prodrugs were considerable more potent.

The new active compounds can be converted in a known manner into the customery formulations, such as tablets, coated tablets, pills, granules, aerosols, syrups, emulsions, suspensions and solutions, using inert, non-toxic, pharmaceutically suitable excipients or solvents. In this connection, the therapeutically active compound should in each case by present in a concentration of about 0.5 to 90% by weight of the total mixture, i.e., in amounts which are sufficient in order to achieve the dosage range indicated.

The formulations are prepared, for example, by extending the active compound with solvents and/or excipients, optionally using emulsifiers and/or dispersants, where, for example, in the case of the use of water as a diluent, organic solvents may optionally be used as auxilary solvents.

Auxiliary solvents which may be mentioned, for example, are: water, non-toxic organic solvents, such as paraffins, (for example, mineral oil fractions), vegetable oils (for example, groundnut/sesame oil), alcohols (for example, ethyl kaolins, aluminas, talc, chalk), ground synthetic minerals (for example, highly disperse silca, silicates), sugars (for example, sicrpse. lactose and dextrose), emulsifiers (for example, polyoxyethylene fatty acid esters, polyoxyethylene fatty alsohol ethers), dispersing agents (for example, ligninsulphite waste liquors, methylcellulose, starch and polyvinylpyrrolidone) and lubricants (for example, magnesium stearate, talc, stearic acid and sodium sulphate).

Administration takes place in a customary manner, preferable orally or parenterally, In particular perlingually or intravenous. In the case of oral administration, tablets may, of course, also contain additions, such as sodium citrate, calcium carbonate and dicalcium phosphate together with various additives, such as starch, preferably potato starch, gelatin and the like in addition to the excipients mentioned. Furthermore, lubricants, such as magnesium stearate, socium lauryl sulphate and talc may additionally be used for tableting. In the case of aqueous suspensions, various flavor improvers or colourants may be added to the active compounds in addition to the abovementioned auxiliaries.

On oral administration, those galenical preparations are to be used in which the release of the active compound initially takes place in the intestine.

Release in the stomach may lead to an undesired premature acidolysis of the substances according to the invention.

In the case of parenteral use, solutions of the active compound may be employed using suitable liquid excipients.

In general, it has proved advantageous on intravenous administration to administer amounts of 0.001 to 1 mg/kg preferably about 0.01 to 0.5 mg/kg of body weight to obtain effective results, and on oral administration the dose is about 0.01 to 20 mg/kg preferably 01. to 10 mg/kg of body weight.

In spite of this, it may be necessary to depart from the amounts mentioned, however, depending on the body weight or the type of administration, but also for reasons of the disorder and its individual behavior towards the medicament or the nature of its formulation and the point in time or interval at which administration takes place.

The foregoing description is offered primarily for purposes of illustration. It will be readily apparent to those skilled in the art that numerous variations in both the formulations and their method of use, not mentioned above, may be made without departing from the spirit and scope of the invention.

We claim:

1. A compound having the formula:

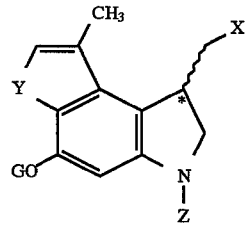

wherein G is a glycosyl moiety; Y is selected from the group consisting of O and NH; X is selected from the group consisting of Cl, Br, or —OSO$_2$CH$_3$ and Z is selected from the group consisting of —SO$_2$—CH$_3$ and —C(O)—R where R is selected from the group consisting of —NHNH$_2$,

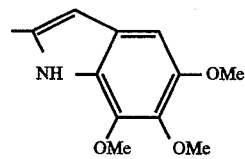

Trimethoxyindole- TMI,

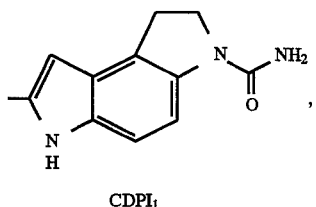

CDPI$_1$

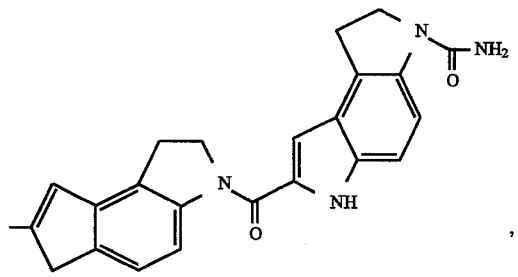

CDPI$_2$

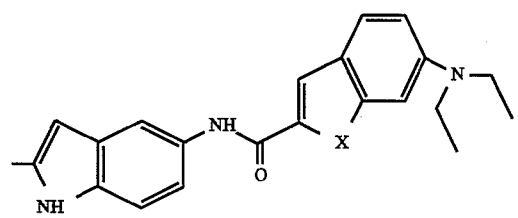

where X=NH, O or S,

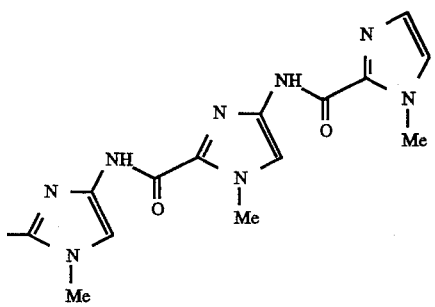

and

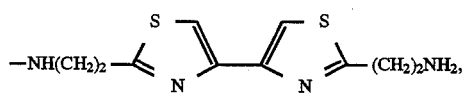

and wherein the asterisk (*) represents an assymmetric carbon giving rise to all optically-active and non-optically-active stereoisomers, as well as racemic and non-racemic mixtures.

2. The compound of claim 1 wherein G is selected from the group consisting of β-galactopyranosyl, β-glucopyranosyluronate and α-mannopyranosyl.

3. A compound of the formula:

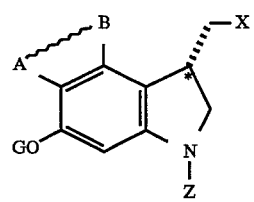

wherein G is a glycosyl moiety, A and B are selected such that when not connected they are both hydrogens and when connected A and B represents a fused benzene ring; X is selected from the group consisting of Cl, Br, or —OSO$_2$CH$_3$ and Z is selected from the group consisting of —SO$_2$—CH$_3$ and —C(O)—R where R is selected from the group consisting of —NHNH$_2$,

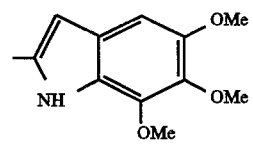

Trimethoxyindole- TMI,

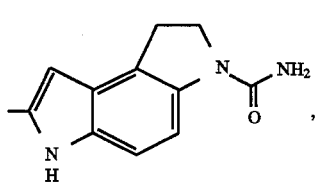

CDPI$_1$

15

-continued

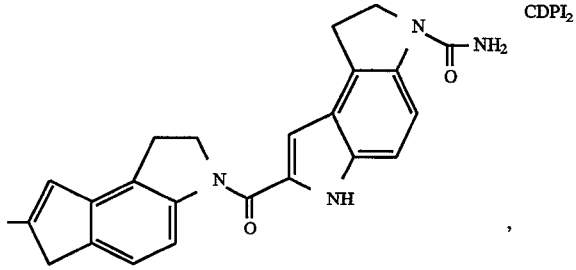

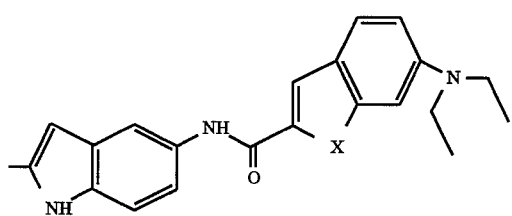

where X=NH, O or S,

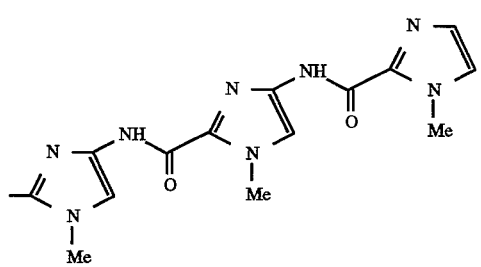

and

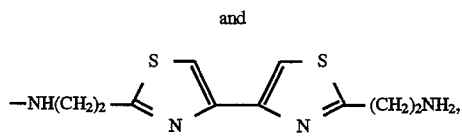

and wherein the asterisk (*) represents an assymmetric carbon giving rise to all optically-active and non-optically-active stereoisomers, racemic and non-racemic mixtures.

4. The compound of claim 3 wherein G is selected from the group consisting of β-galactopyranosyl, β-glucopyranosyluronate and α-mannopyranosyl.

5. The compound of claim 3 wherein A and B are both hydrogens.

6. The compound of claim 3 wherein A and B represents a fused benzene ring.

7. A compound of the formula:

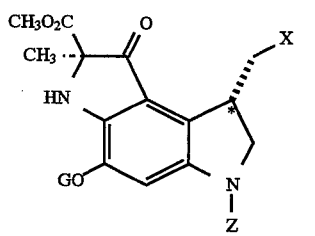

(III)

wherein G is a glycosyl moiety; X is selected from the group consisting of Cl, Br, or —OSO₂CH₃ and Z is selected from the group consisting of —SO₂—CH₃ and —C(O)—R where R is selected from the group consisting of —NHNH₂,

16

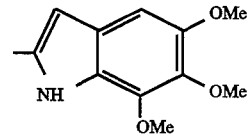

Trimethoxyindole- TMI,

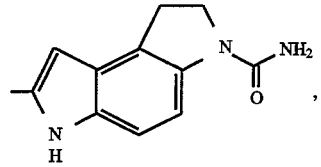

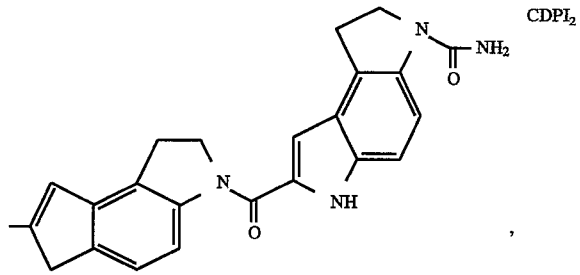

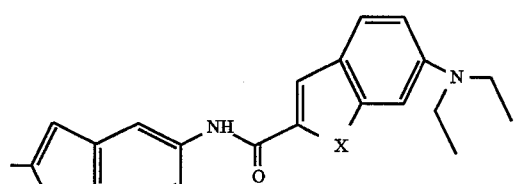

where X=NH, O or S,

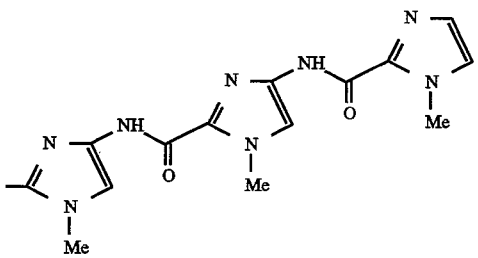

and

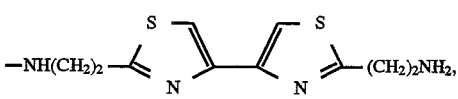

and wherein the asterisk (*) represents an assymmetric carbon giving dse to all optically-active and non-optically-active stereoisomers, racemic and non-racemic mixtures.

8. The compound of claim 7 wherein G is selected from the group consisting of β-galactopyranosyl, β-glycopyranosyl and α-mannopyranosyl.

* * * * *

UNITED STATES PATENT AND TRADEMARK OFFICE
CERTIFICATE OF CORRECTION

PATENT NO. : 5,646,298
DATED : July 8, 1997
INVENTOR(S) : Lutz F. Tietze and Michael J. Powell It is certified that error appears in the above-indentified patent and that said Letters Patent is hereby corrected as shown below:

Front page, Item [75], change Inventor from "Michael J. Powell, Danville, Calif."

to -- Lutz F. Tietze, Göltingen, Germany, and

Michael J. Powell, Danville, Calif. --

Signed and Sealed this

Eighteenth Day of November 1997

Attest:

BRUCE LEHMAN

Attesting Officer     Commissioner of Patents and Trademarks